United States Patent [19]

Phillipps et al.

[11] Patent Number: 4,461,302

[45] Date of Patent: Jul. 24, 1984

[54] COUPLING OF MULTIPLE PHYSIOLOGICAL SIGNALS ACROSS AN ISOLATION BARRIER

[75] Inventors: Patrick G. Phillipps, Wayland, Mass.; Kenneth M. Ma, Yorktown Heights, N.Y.

[73] Assignee: American Home Products Corporation, New York, N.Y.

[21] Appl. No.: 359,971

[22] Filed: Mar. 19, 1982

[51] Int. Cl.³ .............................................. A61B 5/00
[52] U.S. Cl. .................................... 128/630; 128/903; 128/908
[58] Field of Search ............... 128/630, 695, 696, 709, 128/710, 711, 712, 903, 908

[56] References Cited

U.S. PATENT DOCUMENTS 3,888,261   6/1975   Maurer ................................ 128/421
4,044,775   8/1977   McNichols ......................... 128/421

Primary Examiner—William E. Kamm
Attorney, Agent, or Firm—Edward M. Blocker

[57] ABSTRACT

A system for coupling a plurality of physiological signals across an isolation barrier. A plurality of physiological signals received at a number of signal inputs on the isolated side of the barrier are sampled during separate time periods and coupled to the primary winding of a transformer. The direction of signal flow through the primary winding is reversed during each said period. A pair of serial pulses of opposed polarities are induced in the secondary winding for each sampled signal. The pairs of serial pulses induced in the secondary winding are reconverted to the plurality of physiological signals on the non-isolated side of the barrier.

5 Claims, 2 Drawing Figures

COUPLING OF MULTIPLE PHYSIOLOGICAL SIGNALS ACROSS AN ISOLATION BARRIER

BACKGROUND OF THE INVENTION

The present invention relates to systems for coupling a plurality of physiological signals across an isolation barrier.

Patient monitoring instruments commonly provide the capability of monitoring a multiplicity of physiological functions, for example, ECG, respiration, blood pressure, body temperature, etc. Isolated front end circuitry to which the monitoring electrodes are coupled serves to isolate the patient from sources of potentially dangerous electrical power. In one commonly used isolation technique, the primary winding of a transformer is connected to the front end circuitry to receive the input signals and transmit such signals to its secondary winding without providing an electrically conductive path between the front end circuitry and the remaining circuitry of the instrument. To reduce circuit complexity and cost, the input signals are time division multiplexed and then provided to the primary winding to be transmitted to the non-isolated circuitry.

To avoid unacceptably high levels of cross talk between the signals, it is necessary to provide a substantial dead time between signals to dissipate the residual magnetization of the transformer resulting from the signals previously transmitted. Accordingly, in a given system the data rate is limited by the need to introduce such dead time intervals between signals which has the effect of either limiting the number of signals which may be transmitted across the barrier and/or signal bandwidth.

SUMMARY

In accordance with one aspect of the present invention, the system is provided for coupling a plurality of physiological signals across an isolation barrier. The system comprises a plurality of signal inputs for receiving a plurality of physiological signals. A transformer has a primary winding and a secondary winding. Means are provided for sampling each of the physiological signals during separate time periods and coupling each sampled signal to the primary winding such that the direction of signal flow therethrough is reversed during each said period. A pair of serial pulses of opposed polarities are thus induced in the secondary winding for each sampled signal. Means are provided for reconverting the pairs of serial pulses induced in the secondary winding to said plurality of physiological signals. By transmitting each signal from the primary to the secondary as a pair of serial pulses of opposed polarities, the amount of residual magnetization created by each pulse pair is substantially reduced compared with that resulting from single pulse signal transmission. Therefore, it is not necessary to provide long dead time periods between pulses representing different signals to avoid undesirable cross talk. A higher data rate is thus achievable in a given system, making it possible to either increase the number of multiplexed signals, increase the bandwidth of existing channels, or both.

DETAILED DESCRIPTION

Figure 1:
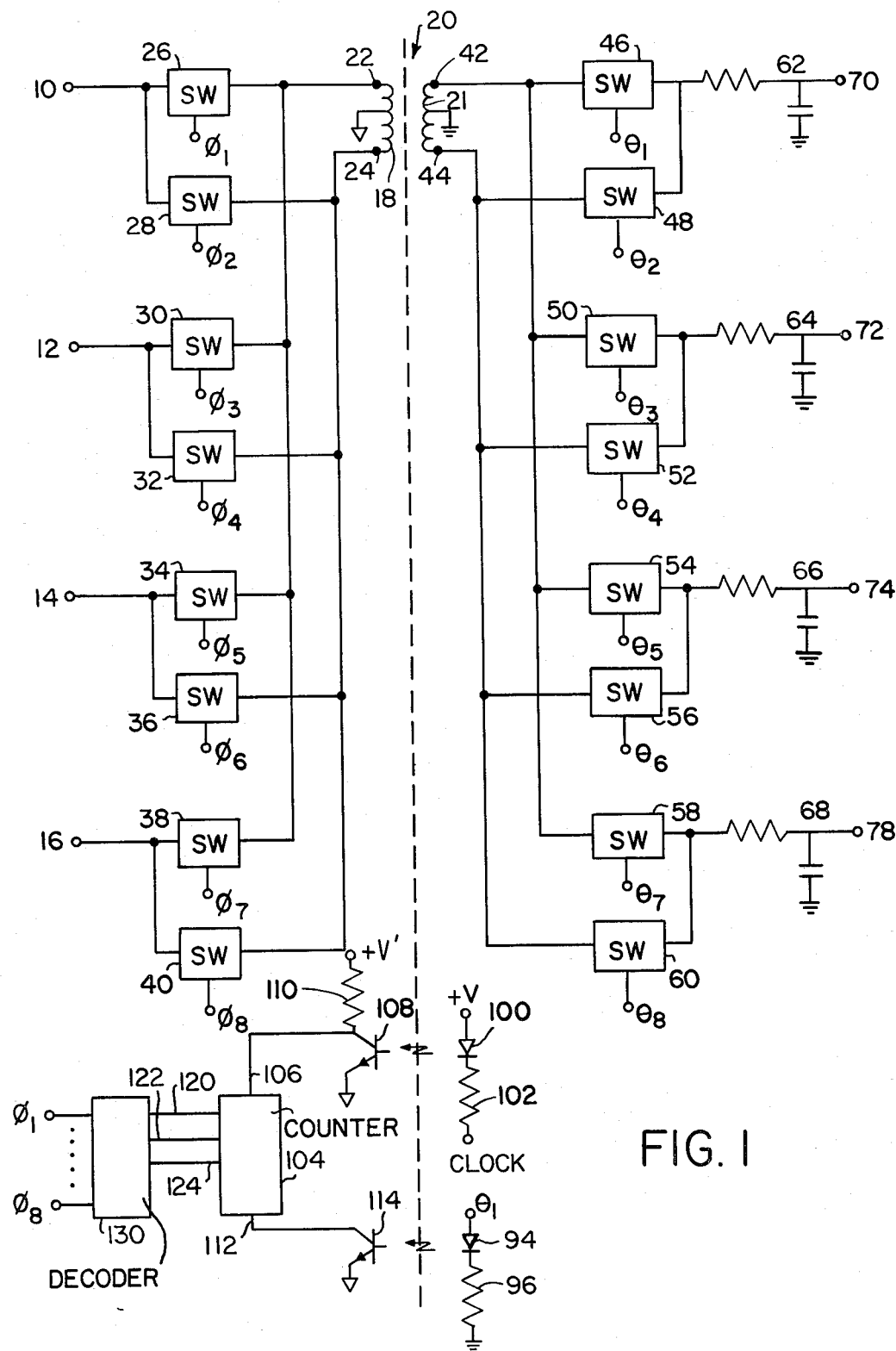
FIG. 1 is a schematic diagram of a system in accordance with the present invention for coupling a plurality of physiological signals across an isolation barrier.

With reference first to FIG. 1, four input terminals are designated 10, 12, 14 and 16. Each of the input terminals is coupled with isolated signal input circuitry to receive respective ones of various physiological signals, such as ECG, respiration, temperature, blood pressure, etc. Each of the signals received at the input terminals is time division multiplexed by a network of electrical switches which provide the thus multiplexed signals to a primary winding 18 of an isolation transformer 20. Primary winding 18 has a center tap connected to floating ground and first and second terminals 22 and 24.

Four pairs of electrical switches are provided: a first pair of switches 26 and 28, a second pair of switches 30 and 32, a third pair of switches 34 and 36 and a fourth pair of switches 38 and 40. Each switch has an input terminal, an output terminal and a control terminal. A given one of switches 26 ... 40, upon receipt of a control signal at its control terminal, responds to couple its input terminal to its output terminal, and in the absence of the control signal provides an open circuit between its input and output terminals.

The input terminals of the switches in the first through fourth switch pairs are connected respectively to input terminals 10, 12, 14 and 16. The output terminals of switches 26, 30, 34 and 38 are all connected to terminal 22 of winding 18, while the output terminals of switches 28, 32, 36 and 40 are all connected to terminal 24. The control terminal of each of switches 26 through 40 is coupled to receive a respective control signal $\phi_1$, $\phi_2 \ldots \phi_8$.

The control signals $\phi_1$ through $\phi_8$ are provided in numerical sequence to the switches 26 and 40 to define 8 separate and sequential intervals of equal duration. Accordingly, during the first interval, the signal received at input terminal 10 will be sampled by switch 26 and coupled thereby to terminal 22 through winding 18 to floating ground through the center tap, and during the second interval the input signal will be sampled by switch 28 and provided thereby to terminal 24 through primary winding 18 to floating ground through the center tap. Accordingly, during the first interval, a pulse proportional in magnitude to the signal received at input terminal 10 will be produced in secondary winding 21, while during the second interval, a second pulse also proportional in magnitude to the input signal at terminal 10 but opposite in polarity to the first pulse will be produced in secondary winding 21. The net effect of the reverse of the direction of current flow through the primary winding 18 is a substantially reduced residual magnetization in the core of transformer 20 compared with that resulting from single pulse signal transmission.

In like manner, the signal received at input terminal 12 is coupled through switches 30 and 32 to the primary winding 18 through terminals 22 and 24, respectively, during the third and fourth intervals, thus to provide a pair of oppositely polarized pulses on secondary winding 21, each pulse being proportional in magnitude to the signal received at input terminal 12. During the fifth and sixth intervals, switches 34 and 36 are actuated in like manner to couple the signal received at input terminal 14 to primary winding 18 thus to produce a corresponding pair of oppositely polarized pulses on secondary winding 21, each pulse being proportional in magnitude to the signal received at input terminal 14. Finally, during the seventh and eighth intervals, switches 38 and 40 are actuated to couple the signal received at input terminal 16 to primary winding 18 thus to produce a fourth pair of oppositely polarized pulses on secondary winding 21 of transformer 20, each pulse being proportional in magnitude to the signal received at input terminal 16.

A secondary winding 21 of transformer 20 has a first terminal 42, a second terminal 44 and a center tap connected to equipment ground on a non-isolated side of the system. The four pulse pairs, each corresponding to a respective one of the signals received on input terminals 10 through 16, are demultiplexed by four pairs of electrical switches. A first such pair of switches comprises switches 46 and 48. Switch 46 has an input terminal connected to terminal 42 of secondary winding 21, while switch 48 has an input terminal connected to terminal 44 of secondary winding 21. Switches 46 and 48 each have output terminals which are connected one to the other. A second pair of switches comprises switches 50 and 52. Switch 50 has an input terminal connected to terminal 42 of secondary winding 21, while switch 52 has an input terminal connected to terminal 44 of secondary winding 21. Switch 50 has an output terminal connected to an output terminal of switch 52. A third pair of switches comprises switches 54 and 56. Switch 54 has an input terminal connected to terminal 42, while switch 56 has an input terminal connected to terminal 44. Switch 54 has an output terminal connected to an output terminal of switch 56. A fourth pair of switches comprises switches 58 and 60. Switch 58 has an input terminal connected to terminal 42, while switch 60 has an input terminal connected to terminal 44. Switch 58 has an output terminal connected to an output terminal of switch 60. Four low pass filters designated 62, 64, 66 and 68 each comprise the serial connection of a resistor and filtering capacitor, a first terminal of each resistor being connected to both output terminals of a respective pair of switches 46 and 48, 50 and 52, 54 and 56 and 58 and 60. A first terminal of the filter capacitor of each low pass filter is connected to the second terminal of its respective resistor, while the second terminal of the filter capacitor is connected to equipment ground. Each of low pass filters 62, 64, 66 and 68 has a respective output terminal 70, 72, 74 and 78 connected to the second terminal of the resistor and the first terminal of the filter capacitor of each filter.

Each of switches 46 through 60 has a control terminal coupled to receive a respective one of a second series of sequential control signals $\theta_1, \theta_2, \ldots \theta_8$. Upon receipt of its respective control signal, each switch is rendered operative to couple its input terminal to its output terminal and in the absence of its control signal, each switch provides an open circuit between its input and output terminals. The signals $\theta_1$ through $\theta_8$ are synchronized with the control signals $\phi_1$ through $\phi_8$ such that signals $\theta_1$ through $\theta_8$ are provided sequentially to the control terminals coincidentally with the first through eighth intervals, respectively. Accordingly, the following switches will be rendered conductive coincidentally and in the following sequence: switches 26 and 46, 28 and 48, 30 and 50, 32 and 52, 34 and 54, 36 and 56, 38 and 58, and 40 and 60.

Since switches 46 and 48 are rendered conductive coincidentally with switches 26 and 28, respectively, the pulses of opposed polarity produced on secondary winding 21 during the first two intervals are reconverted to the original signal received at input terminal 10 during the first two intervals. In the same manner, switches 50 and 52 are rendered conductive coincidentally with switches 30 and 32, respectively, during the third and fourth intervals to reconstruct the signal received at input terminal 12 at the coupled output terminals of switches 50 and 52. In the same manner, switches 54 and 56 coact with switches 34 and 36 to produce at the coupled output terminals of switches 54 and 56 the signal received at input terminal 14 during the fifth and sixth intervals. Lastly, switches 58 and 60 coact with switches 38 and 40 to reconstruct at the coupled output terminals of switches 58 and 60 the signal received at the input terminal 16 during the seventh and eighth intervals. Low pass filters 62 through 68 serve to smooth the signals provided at the output terminals of switches 46 through 60 thus to produce at output terminals 70 through 78 respective signals proportional to the signals received at input terminals 10 through 16.

Figure 2:
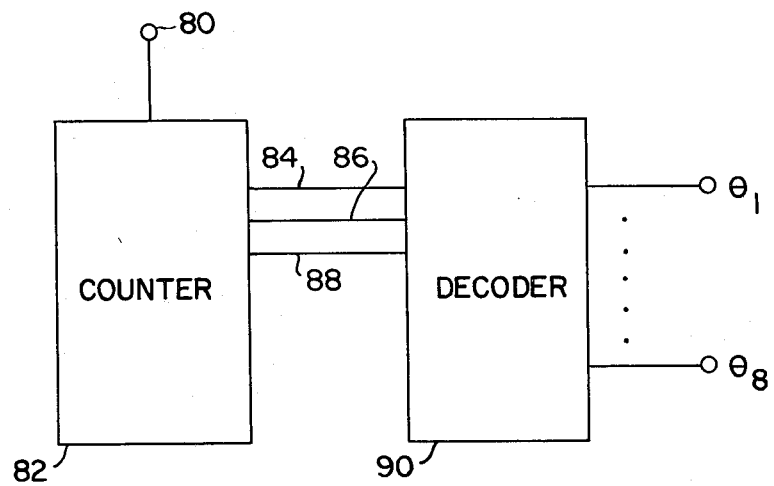
FIG. 2 is a schematic diagram of a circuit useful for generating synchronization signals for use in the system of FIG. 1.

Circuitry appropriate for producing the synchronized control signals $\phi_1$ through $\phi_8$ and $\theta_1$ through $\theta_8$ is described with reference to FIGS. 1 and 2. As shown in FIG. 2, a clock signal is provided to a clock input terminal 80 of a divide-by-eight counter 82. The clock signal may be, for example, a 40 kHz pulse train. Counter 82 converts the clock signal thus received to a three-bit word provided on three output terminals 84, 86 and 88. Terminals 84, 86 and 88 are connected to corresponding input terminals of an octal decoder 90 which serves to convert the binary word thus received to the control signals $\theta_1$ through $\theta_8$ and provides the control signals on eight respective output terminals thereof. The output terminals of decoder 90 are connected with respective control terminals of switches 46 through 60 of FIG. 1 to provide the control signals $\theta_1$ through $\theta_8$ thereto.

The control signal $\theta_1$ is also coupled on the non-isolated side to the anode of a light emitting diode (LED) 94. The cathode of LED 94 is connected to a first terminal of a current limiting resistor 96, whose second terminal is connected to equipment ground. A second light emitting diode (LED) 100 has its anode connected to a source of positive voltage $+V$ and its cathode connected to the first terminal of a current limiting resistor 102. A second terminal of resistor 102 is connected to receive the clock signal. A second divide-by-eight counter 104 located on the isolated side of the barrier has a clock terminal 106 connected to the collector of an NPN phototransistor 108. Transistor 108 has its emitter connected to isolated ground. The collector of transistor 108 is also connected to the first terminal of a resistor 110. A second terminal of resistor 110 is connected to a source of positive voltage $+V'$ provided by an isolated power source (not shown). Transistor 108 is mounted adjacent to LED 100 to receive the light emitted thereby. Counter 104 also has a reset terminal 112 connected to the collector of a second NPN phototransistor 114. Transistor 114 has its emitter connected to isolated ground. Transistor 114 is mounted in proximity to LED 94 to receive light emitted thereby.

LED 100 will respond to the clock signals to produce a series of light pulses received by transistor 108 which in turn responds to reproduce a series of pulses synchronized with the clock signal and provided to counter 104 at its clock input terminal 106. Counter 104 responds to the clock signal to produce a three-bit word provided on three output terminals 120, 122 and 124. LED 94 responds to signal $\theta_1$ to produce a light pulse received by transistor 114 which in turn responds to produce a reset pulse at terminal 112 of counter 104. Accordingly, counter 104 will be reset coincidentally with control signal $\theta_1$ which is selected as the output signal produced by decoder 90 upon the reset of counter 82. The three-bit signal produced by counter 104 is, therefore, synchronized with that produced by counter 82. Terminals 120, 122 and 124 are connected to the input terminals of a second octal decoder 130. Decoder 130 has eight output terminals at which it provides the control signals $\phi_1$ through $\phi_8$ in response to the three-bit signal provided by counter 104. Signal $\phi_1$ is selected to coincide with the reset of counter 104. In this fashion, the control signals $\phi_1$ through $\phi_8$ are produced in synchrony with signals $\theta_1$ through $\theta_8$, respectively.

The system of the present invention may also be utilized to couple a plurality of differential physiological signals across an isolation barrier. For example, the system of FIG. 1 may be so adapted by eliminating the center tap connections of transformer 20. A plurality of differential signals are applied across the primary winding during a series of respective time periods, such that the direction of signal flow is reversed during each period. The signals are suitably demultiplexed and filtered on the non-isolated side of the system. Where power for operating the isolated circuitry is transmitted across the barrier, for example, by a second transformer, the power supply frequency may be used for synchronizing the multiplexing and demultiplexing operations.

It will be appreciated that the system in accordance with the present invention serves to couple a desired number of a patient's physiological signals from the primary winding of a transformer to its secondary winding thus to provide a barrier to the conduction of an electric current and to isolate the patient from potentially dangerous electrical shock. By reversing the direction of signal flow through the primary winding of the transformer in the case of each signal thus transmitted, the residual magnetism produced by each signal is minimized thus to facilitate a relatively high data rate. The system in accordance with the present invention, therefore, provides the capability of accommodating a relatively large number of channels for physiological signals and/or increased signal bandwidth. It will also be appreciated that the present invention is not limited to a system of four channels but is adapted for the coupling of an arbitrarily selected number of isolated physiological signals to non-isolated circuitry.

The terms and expressions which have been employed are used as terms of description and not of limitation, and there is no intention in the use of such terms and expressions of excluding any equivalents of the features shown and described, or portions thereof, it being recognized that various modifications are possible within the scope of the invention claimed.

We claim:

1. A system for coupling a plurality of physiological signals across an isolation barrier comprising:
    means for receiving a plurality of physiological signals;
    isolating transformer means for providing said isolation barrier between a primary winding and secondary winding thereof;
    means for sampling each of the physiological signals during separate time periods for reducing residual magnetization in the isolating transformer means so as to minimize dead time between sampled signals; and
    means for producing a plurality of output signals, each output signal proportional to one of said plurality of physiological signals and produced in response to secondary winding signals generated across the secondary winding.

2. A system as in claim 1; wherein said means for sampling comprises primary switching means for reversing the direction of current flow in the primary winding during each of said separate time periods and wherein each of the secondary winding signals comprises a pair of serial pulses of opposed polarities.

3. A system as in claim 2; wherein the sampling means include means for reversing the direction of current flow in the primary winding at the mid-point of each of said separate time periods.

4. A system as in claim 3; wherein said system further comprises a floating ground; and wherein said primary winding has first and second ends and a center tap connected to the floating ground, and wherein the coupling means couples each sampled, physiological signal from one of the first and second ends to the other during each period.

5. A system as in claim 4; wherein said system further comprises a ground and wherein the secondary winding has first and second ends and a center tap, said center tap being connected to said ground and wherein said means for producing a plurality of output signals comprises a plurality of output terminals and secondary switching means for switching the plurality of output terminals from one of the first and second ends of said secondary winding to the other coincidentally with the reversing of current flow direction in the primary winding and low pass filtering means for smoothing the plurality of output signals provided at the output terminals of the secondary switching means.

* * * * *